United States Patent [19]
Farahi et al.

[11] Patent Number: 6,050,656
[45] Date of Patent: Apr. 18, 2000

[54] OPTICAL BASED OPACITY AND FLOW MONITORING SYSTEM AND METHOD OF MONITORING OPACITY AND FLOW

[75] Inventors: Faramarz Farahi, Concord; Terrill W. Mayes, Charlotte, both of N.C.

[73] Assignee: University of North Carolina at Charlotte, Charlotte, N.C.

[21] Appl. No.: 08/956,728

[22] Filed: Oct. 23, 1997

[51] Int. Cl.[7] .................................................. G01N 21/61
[52] U.S. Cl. ............................................................... 306/439
[58] Field of Search .................................... 356/437, 438, 356/439, 28, 434

[56] References Cited

U.S. PATENT DOCUMENTS

| | | | |
|---|---|---|---|
| 3,864,577 | 2/1975 | Pellett et al. | 356/136 |
| 3,885,162 | 5/1975 | Geertz | 356/439 |
| 4,027,981 | 6/1977 | Steinbatz | 356/434 |
| 4,201,467 | 5/1980 | Hartmann et al. | 356/28 |
| 5,131,741 | 7/1992 | Zweben | 356/28 |
| 5,610,704 | 3/1997 | Berzins et al. | 356/437 |
| 5,748,325 | 5/1998 | Tulip | 356/437 |

*Primary Examiner*—Richard A. Rosenberger
*Attorney, Agent, or Firm*—Dougherty & Associates

[57] ABSTRACT

A pollutant emissions monitoring system and a method of measuring pollutant emissions, particularly fly ash, of gas passing through stacks of coal-fired boilers. An all optical-based emission monitor has an opacity monitor and a flow rate monitor connected to a remote data processing facility by a single fiber optic cable. A timing/calibration wheel assembly initiates measurement cycles and calibrates the opacity monitor. A first beamsplitter polarizes a collimated light beam from a light source into two collimated light beams, an upstream and a downstream beam. A second beamsplitter receives the collimated light beams, reflects a portion of the light beams to the flow rate monitor and passes the remainder of the light beams to a retro-reflector. The remote data processing facility determines the flow rate of the fly ash by measuring a plurality of pairs of upstream and downstream flow signals transmitted from the flow rate monitor, correlating each of the plurality of pairs of flow signals, normalizing the correlated flow signals and summing the normalized flow signals. The retro-reflector returns the remainder of the light beams to the opacity monitor. The remote data processing facility determines opacity by calculating optical density values based on a diffuser intensity, an offset intensity and a reflected intensity measured by the opacity monitor.

20 Claims, 9 Drawing Sheets

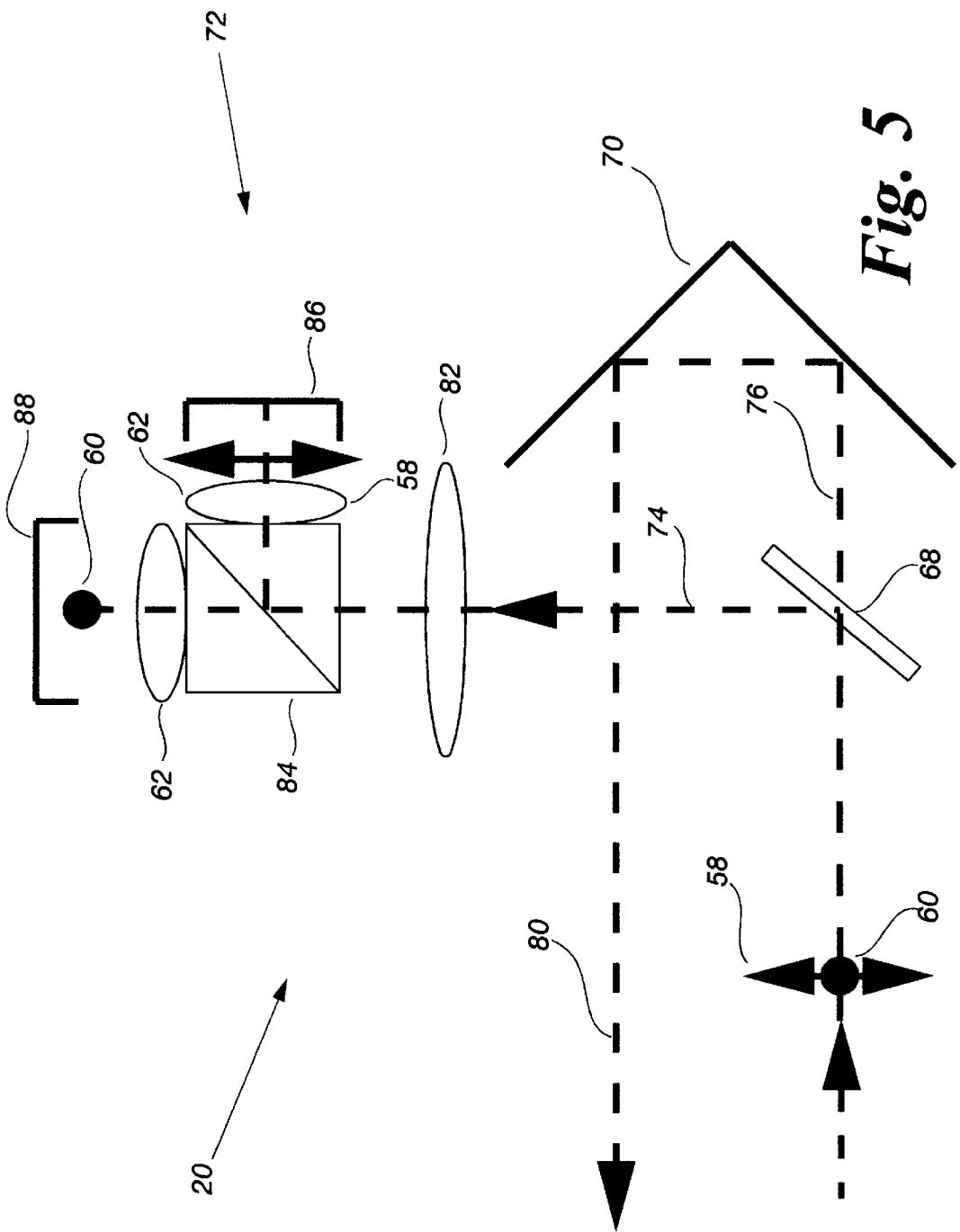

6,050,656

OPTICAL BASED OPACITY AND FLOW MONITORING SYSTEM AND METHOD OF MONITORING OPACITY AND FLOW

FIELD OF THE INVENTION

The present invention relates to an optical based pollutant emissions monitoring system and method of monitoring pollutant emissions, and more particularly to an optical based opacity and flow monitoring system for pollutant emissions and method of measuring the opacity and flow rate of pollutant emissions generated as a by-product of industrial activity.

BACKGROUND OF THE INVENTION

Environmental Protection Agency (EPA) regulations require that industries continuously monitor the emission of atmospheric and water pollutants generated as by-products of industrial activity. Of central concern is the emission of fly ash from the stacks of coal-fired boilers. Determination of the weight of fly ash produced as by-product requires two separate measurements: (1) a measurement of the particulate density of the stack gases; and (2) a measurement of the volumetric flow rate of the gases passing through the stack. As defined herein, "opacity" is the fraction of incident light which is lost in transmission through an optical medium. Currently, the standard method of measuring particulates contained in stack gases is optical transmissometry where the opacity of stack gases is determined. The product of particulate density and flow rate yields the weight per unit time of fly ash emitted into the environment from a unit cross-sectional area of the stack.

Optical measurements of particle velocity are widely used in studies of gas flows and also in particle dynamics. One well-known velocity measurement technique is laser Doppler velocimetry, also known as laser Doppler anemometry. According to this approach, particles or other elements simultaneously scatter light from two coherent beams, each of the beams having different angles of incidence. A photodetector receives the light and generates a frequency representing the heterodyne difference in Doppler shift frequencies produced by the motion of the particles relative to the beams. Laser Doppler velocimetry is useful but requires careful alignment of the beams as well as maintenance of beam coherency.

Another well-known velocity measuring technique is time-off-light velocimetry, also referred to as transit time, two-spot, or two-focus velocimetry. According to this method, two beams of electromagnetic radiation with radially symmetrical intensity distributions are directed through a particle sampling volume. A particle, when passing through both beams, generates two pulse signals corresponding to each beam. A timing signal is initiated, coincident with the first pulse, and terminated, coincident with the second pulse, for an open "time-of-flight" measurement over a known distance, thus yielding a particle velocity. This approach provides better signal-to-noise ratios than laser Doppler velocimetry for certain applications and does not require laser light beam coherence. Further, since time-of-flight velocimetry involves measuring time rather than frequency, the typical time-off-light application can employ lower cost, signal processing circuitry.

However, time-of-flight velocimetry is subject to error. For example, a particle can produce a signal sufficient for detection when passing through one of the beams, but not the other, either due to the particle's trajectory or the particle's size being at the borderline of detection by the other beam. This occurrence can lead to an erroneous time-of-flight measurement when a signal from the arrival of a second particle is mistakenly identified as the departure signal of the first particle.

Several emissions monitoring systems, currently available, can separately determine the opacity and flow rate of stack emissions. A major shortcoming of such systems is that opacity is determined using a stand-alone, optical-based monitoring system, while flow rate is determined using an independent, acoustically-based monitoring system. These two systems are typically supplied by different companies and use technologies that are dissimilar. One measurement necessarily requires the other measurement in order to determine emission of fly ash, and the costs of not just one but both monitoring systems must also be considered.

Additionally, emissions monitoring systems currently on the market require four stack penetrations: two stack penetrations for the opacity monitor, and two more stack penetrations for the flow monitor. Because current flow monitors determine flow rate of stack gases by measuring a differential time-of-flight of two ultrasound waves (e.g., one wave traveling with the flow, the other wave travelling against the flow), the two stack penetrations for the flow monitor must be displaced along the length of the stack.

Current emissions monitoring systems also pose another problem in that the current systems transfer opacity and flow rate data collected by stack mounted units to a remote data processing station using electrically conducting cable. Utilization of electrically conducting cable for data transfer results in systems with significant susceptibility to damage by lightning. Not only can lightning destroy stack mounted units, electrical surges conducted to remote monitoring stations by the conducting cable can also destroy the remote equipment used to analyze and store collected data. As a result, lightning can damage and disable the typical current emissions monitoring system in its entirety.

Damage from lightning to current emissions monitoring systems can occur even if the stack mounted unit does not experience a direct lightning hit. Stacks are often separated from remote monitoring stations by distances of a thousand meters or more. Lightning strikes in the vicinity of a stack can produce voltage surges on the conducting cable connecting the stack-mounted units to the remote monitoring site that are large enough to damage electrical equipment.

What are needed are an optical based opacity and flow monitoring system for pollutant emissions and a method of measuring opacity and flow rate of pollutant emissions. Also, an opacity and flow monitoring system for pollutant emissions is needed that is substantially immune to electrical surge resulting from lightning strikes on or near an industrial emissions stack.

SUMMARY OF THE INVENTION

The invention provides an optical based opacity and flow monitoring system for pollutant emissions and a method of measuring opacity and flow rate of pollutant emissions. The invention further provides an opacity and flow monitoring system for pollutant emissions that is substantially immune to electrical surge resulting from lightning strikes on or near an industrial emissions stack. The system described herein uses optical fiber, an electrical insulator, for data transfer between a remote data processor and a stack-mounted opacity/flow rate monitor. The system described herein determines both opacity and flow rate using a single, entirely optical unit requiring only two diametric stack penetrations. The entirely optical unit accurately measures opacity and tracks variable flow rates.

Utilization of optical fiber eliminates electrical surge problematic of electrically conducting cable. Light from a light beam source housed in a first assembly is collimated and directed through a first stack port toward a second assembly mounted at a second stack port on the opposite side of the stack. A portion of the light arriving at the second assembly is extracted from the light beam and encoded for transmission via optical fiber to a remote data processor where flow rate data is computed and stored. The remainder portion of the light beam arriving at the second assembly is retro-reflected to the first assembly where the retro-reflected light beam is optically encoded for transmission to a remote data processor. The remote data process or processes and stores the optically encoded retro-reflected light beam as opacity data.

The only connection between the stack an d the remote data processor is a single optical cable. This optical cable has four optical fibers. Two optical fibers transmit flow rate data, one optical fiber transmits opacity data. The fourth fiber transmits a timing signal that synchronizes the remote data processor and the stack mounted assemblies.

The optical based system described herein is easily multiplexed to have multiple opacity/flow rate assemblies operating simultaneously without additional optical fiber cable and remote processing facilities. For example, in a typical steam plant having multiple boilers and multiple stacks, where each boiler is served by a separate stack, and the multiple stacks are spaced over a distance which may exceed 1000 meters, optical fiber easily connects together opacity/flow rate assemblies on each of the stacks. These fibers, when cabled together, allow the transmission of flow rate and opacity data for the multiple stacks to the remote data processor on a single optical fiber cable.

OBJECTS OF THE INVENTION

The principal object of the present invention is to provide an emissions monitoring system that measures opacity and flow rate of pollutant emissions using entirely optical based monitors.

Another object of the invention is to provide a two-pass pollution emissions monitoring system having a continuously recording opacity monitor that exhibits excellent stability against noise and signal drift resulting from vibrations and thermally induced expansion within the system being monitored.

Another object of the invention is to provide an optical based flow monitor that measures variable flow velocities of gases passing through a stack having laminar or turbulent flow characteristics.

Another object of the invention is to provide an optical based pollutant emissions monitoring system having an opacity/flow rate monitor that is stack-mounted as a single unit.

Another object of the invention is to provide a pollutant emissions monitoring system that is substantially immune to damage caused by lightning and electrical surge, particularly from lightning strikes on or near a stack.

Another object of the invention is to provide a method of measuring opacity and flow velocities of pollutant emissions that naturally yields line of sight averages as opposed to measurements at a point.

BRIEF DESCRIPTION OF THE DRAWINGS

The foregoing and other objects will become more readily apparent by referring to the following detailed description and the appended drawings in which:

FIG. 5 is a top view of a second assembly of a pollutant emission monitor in accordance with the present invention.

DETAILED DESCRIPTION

The system and method described hereinafter contain features required by the EPA for use in environmental monitors applied in the electric power industry.

Figure 1:
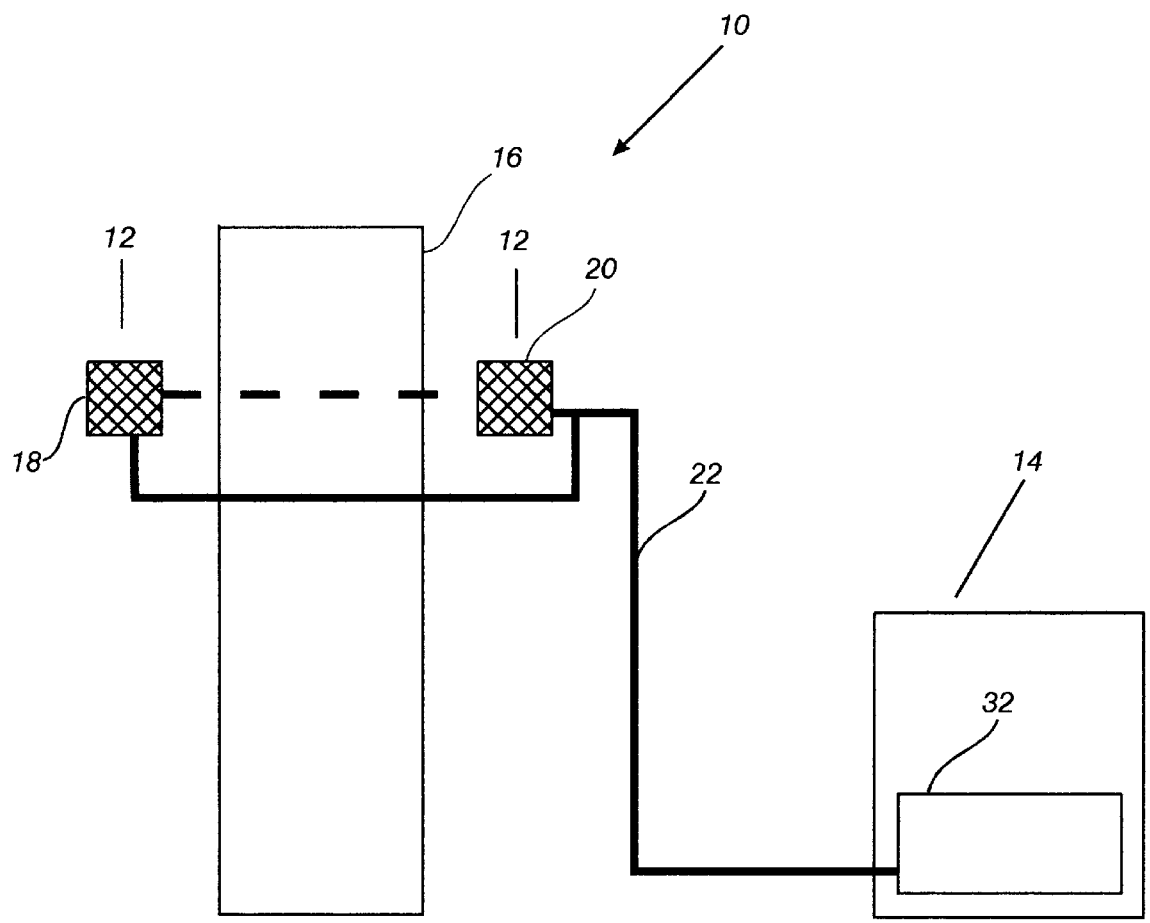
FIG. 1 is a schematic diagram of an optical based pollutant emissions monitoring system in accordance with the present invention.

Referring now to the drawings, and particularly to FIG. 1, a pollutant emissions monitoring system, indicated generally at 10, includes an entirely optical-based emission monitor 12 that is electrically isolated from a remote data processing facility 14. The emission monitor 12 is mounted on a stack 16 and measures an opacity and a flow rate of gas passing through the stack. A fiber optic cable 22 connects the emission monitor 12 to the remote data processing facility 14 and conducts optical data from the emission monitor to a remote data processor 32 located in the remote data processing facility 14. Although developed to monitor emissions from the stacks of coal fired boilers, the system and method described herein can be applied in any application where the information desired is a simultaneous determination of opacity and flow rate.

Figure 2:
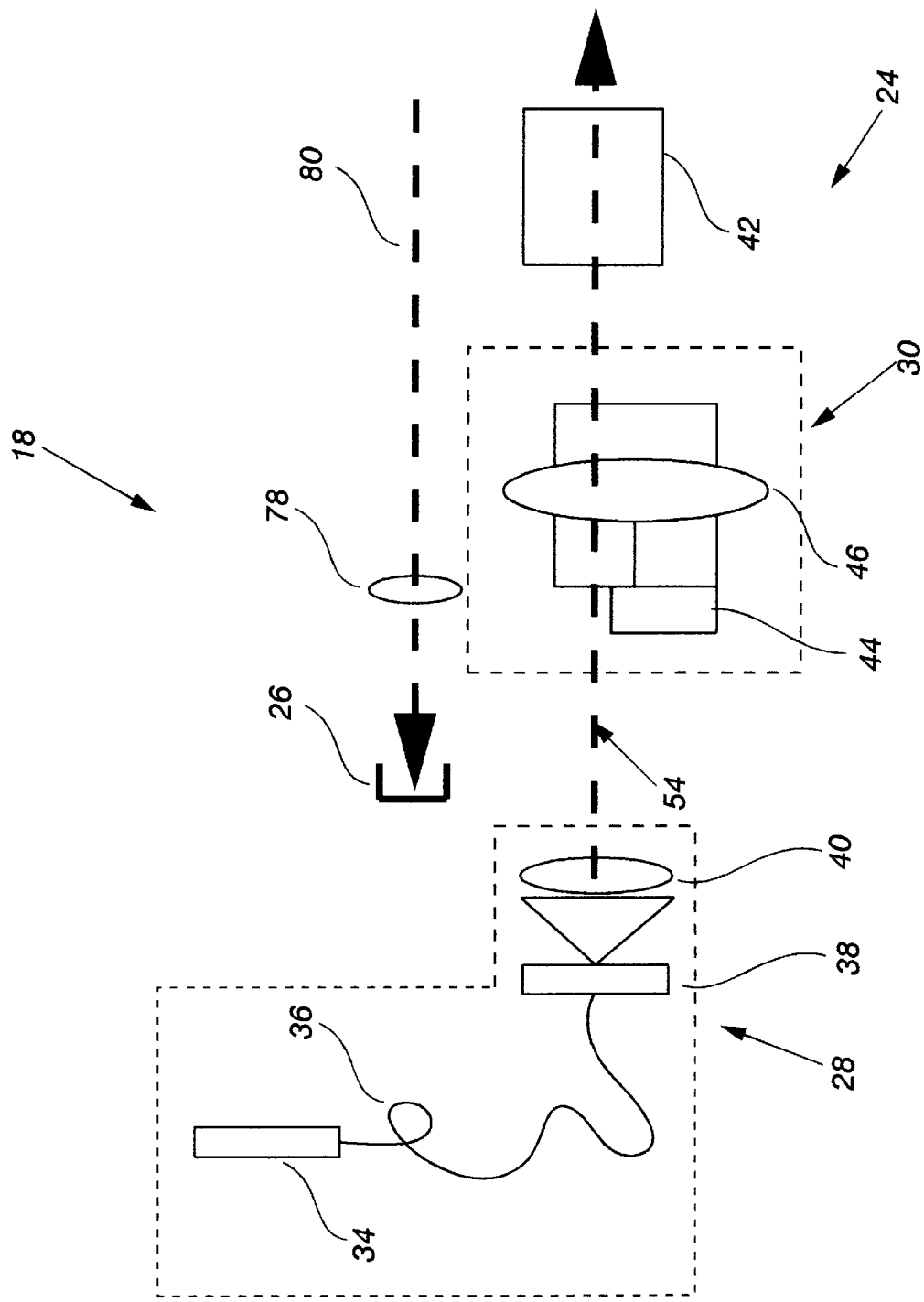
FIG. 2 is a top view of a first assembly of a pollutant emission monitor in accordance with the present invention.

The emission monitor 12 comprises a first assembly 18 and a second assembly 20. FIG. 2 is a top view of the first assembly 18. The first assembly 18 houses a light beam assembly, indicated generally at 24, an opacity monitor 26 and the requisite electronics (not shown) needed to power the light beam assembly, operate the opacity monitor and encode opacity data for transmission to the remote data processing facility 14 or a computer (not shown) in the remote data processing facility. The light beam assembly 24 has a light source, indicated generally at 28, a timing/calibration wheel assembly, indicated generally at 30, that is optically connected to the remote data processor 32 and a first beamsplitter 42.

The light source 28 comprises a diode laser 34 for producing a light beam, a single mode optical fiber 36 coupled to the diode laser 34, an x-y positioner 38 connected to the single mode optical fiber 36 and a lens 40. The diode laser 34 generates a light beam 54 and, preferably, is a 10 mW diode laser operating at a wavelength of about 678 nm. In an alternative embodiment, the diode laser 34 is a pulsed laser that generates a pulsed light beam that minimizes optical noise problems produced by ambient light. The x-y positioner 38 receives the light beam 54 from the diode laser 34 and directs the beam to a pre-determined position across the stack. In a preferred embodiment, the x-y positioner 38 directs the beam across the stack to the second assembly 20. The lens 40 of the light source 28 collimates diverging light of the light beam 54 which emerges from the single mode optical fiber 36 and is directed by the x-y positioner 38.

Figure 3:
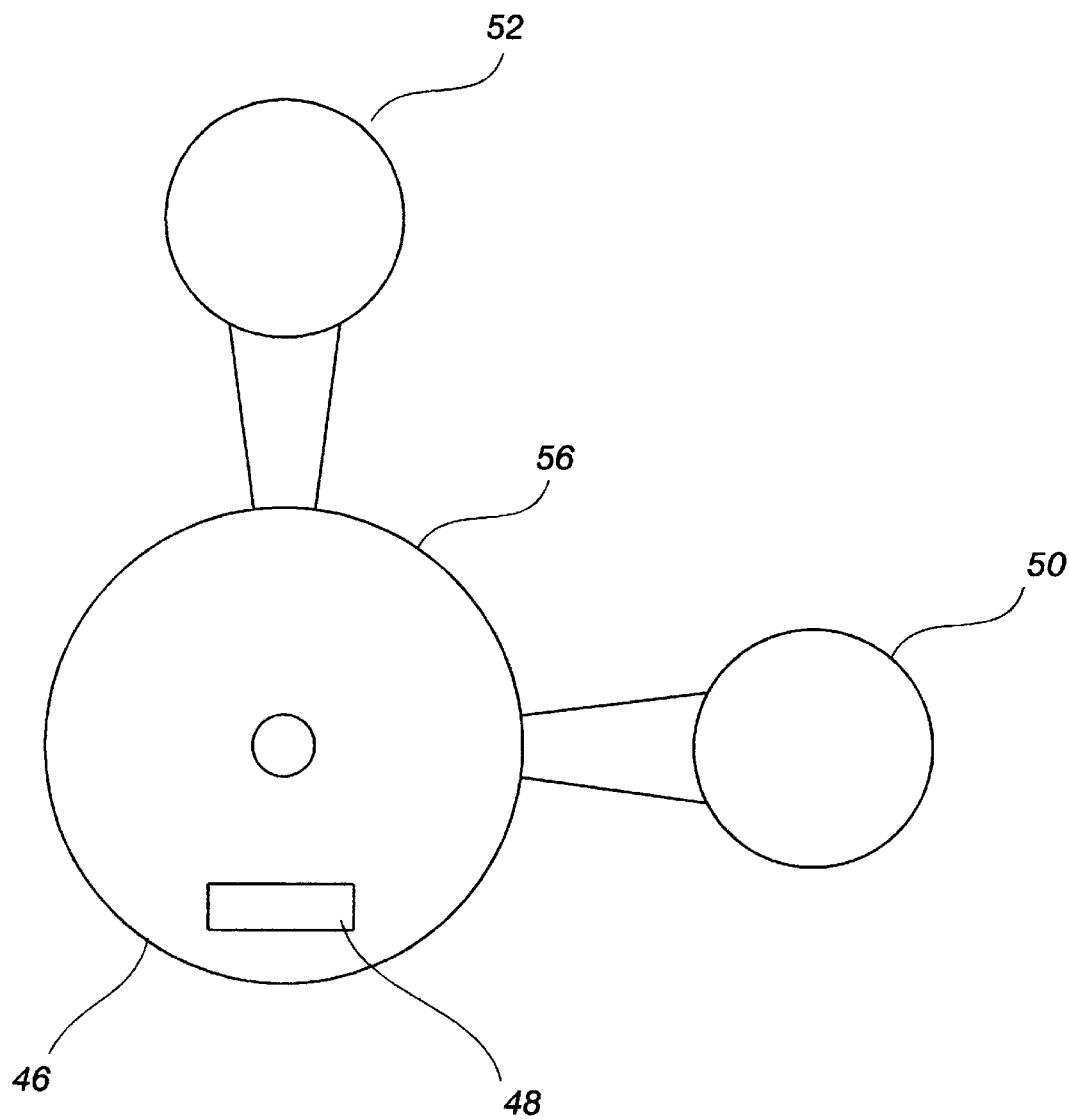
FIG. 3 is a front view of a portion of a timing/calibration wheel assembly of a pollutant emission monitor in accordance with the present invention.

The timing/calibration wheel assembly 30 has a synchronous motor 44, a timing wheel 46 fixed to the synchronous motor 44 and a light emitter/detector (not shown) optically coupled to the timing wheel 46. FIG. 3 is a front view of a portion of the timing/calibration wheel assembly 30. As best shown in FIG. 3, the timing/calibration wheel assembly 30 additionally includes a diffuser 50 mounted on the timing wheel 46 and an optical absorber 52 mounted on the timing wheel 46. The diffuser 50 and the optical absorber 52 produce optical signals for real-time calibration of the opacity monitor 26, described hereinafter, by the emissions monitoring system 10. The wheel assembly 30 initiates measurement cycles by generating an optical signal once each revolution of the synchronous motor 44 to inform the remote data processor 32 of a beginning of a new measurement cycle.

The synchronous motor 44 generates a pre-determined constant rate of revolution. Preferably, the synchronous motor 44 generates a rate of revolution of about 2 revolutions/minute. The timing wheel 46 has a front side 56, a back side (not shown) and a timing slot 48. The light emitter/detector has an emitter portion facing the front side 56 of the timing wheel 46 and a detector portion facing the back side of the timing wheel 46. The detector portion is aligned with the emitter portion and the timing slot so that when the timing slot moves between the emitter portion and the detector portion, an optical signal is generated by the light emitter/detector corresponding to each revolution of the synchronous motor 44.

The opacity monitor 26 measures optical density, D, of stack gas. The optical density is used to determine an opacity, O, which is related directly to a particulate density of the stack gas. In a two-pass system, D is determined from light intensity measurements by the equation, $$D = \tfrac{1}{2} \text{Log}_{10} I_O / I_S. \qquad \text{Eq. (1)}$$

$I_O$ is a sample beam intensity before the sample light beam enters the stack region, and $I_S$ is a sample light beam intensity after the sample light beam has crossed the stack 16 and returned. A factor of ½ appears in Eq. (1) to account for a two-pass system. Opacity is related to D by $$O = 1 - 10^{-D}. \qquad \text{Eq. (2)}$$

During operation of the system and method described herein, the value of $I_O$ in Eq. (1) is not directly measurable. However, $I_O$ is calculated from the intensity, $I_D$, of light reflected into the opacity monitor 26 by the diffuser 50. The diffuser 50 is preferably an opal diffuser. Before the emission monitor 12 is mounted on a stack, the first assembly 18 and the second assembly 20 are placed in a clean-air environment and separated by a distance equal to the diameter of the stack on which the emission monitor is to be mounted. The ratio $I_{CO}/I_{DO}$, where $I_{CO}$ is the clear air sample beam intensity and $I_{DO}$ is the calibration diffuser intensity, is measured. The ratio $I_{CO}/I_{DO}$, defined hereinafter as the calibration constant, does not change unless the geometry of the optical components in the first assembly 18 or the second assembly 20 is changed or optical surfaces in the emission monitor 12 become dirty. During operation, $I_O$ in Eq. (1) is determined from $$I_O = I_D \, I_{CO}/I_{DO} \qquad \text{Eq. (3)}$$

Figure 4:
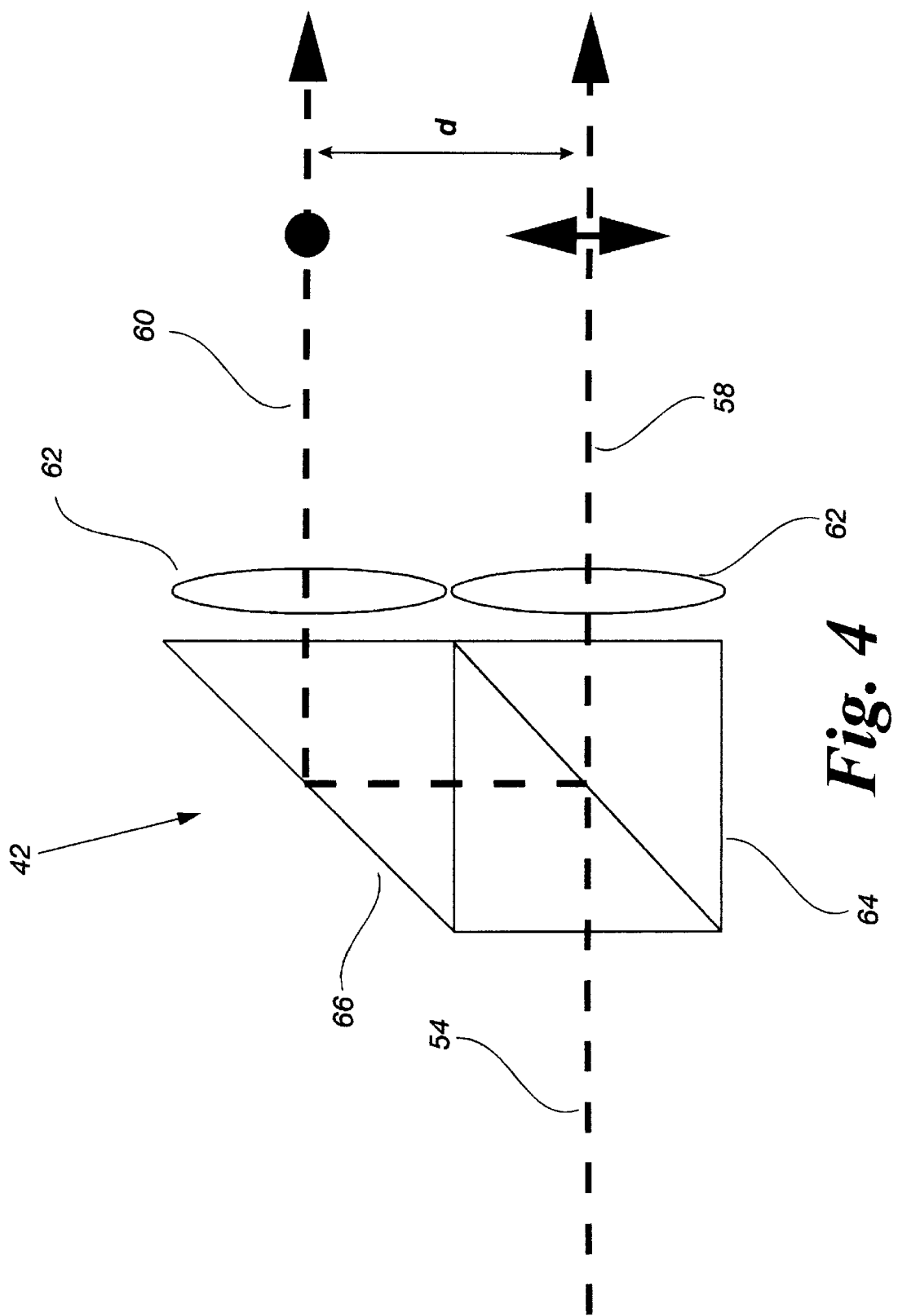
FIG. 4 is a side view of a portion of a first beamsplitter of a pollutant emission monitor in accordance with the present invention.

FIG. 4 is a side view of a portion of the first beamsplitter 42. The first beamsplitter 42 receives the collimated light beam 54, originating from the light source 28 (FIG. 2) and passing through the wheel assembly 30 (FIG. 2), and separates the 25 collimated light beam 54 into two collimated beams, an upstream beam 58 and a downstream beam 60. The upstream beam 58 and the downstream beam 60 are separated vertically by a pre-determined distance, d, and are used to determine the flow rate. In a preferred embodiment of the present invention, the first 30 beamsplitter 42 has a first pair of polarizers 62 mounted on a beamsplitter cube 64 and a reflecting prism 66 to produce orthogonal polarizations of the two beams, as best shown in FIG. 4. The upstream beam 58 is preferably vertically polarized and the downstream beam 60 is preferably horizontally polarized.

The two collimated beams, the upstream beam 58 and the downstream beam 60, cross the diameter of the stack 16 (FIG. 1) and enter the second assembly 20, as shown in FIG. 5, at a diametric position on the stack 16 and across from the first assembly 18. FIG. 5 is a top view of the second assembly 20. The second assembly 20 has a second beamsplitter 68, a retro-reflector 70 aligned with the second beamsplitter 68 and a flow rate detector, indicated generally at 72. The second beamsplitter 68 is preferably a 70/30 beamsplitter so that a portion 74 of the light beam 54 from the first assembly 18 (FIGS. 1 and 2), preferably about 70% of the light beam 54, is deflected toward the flow rate detector 72 by the second beamsplitter 68. The remainder 76 of the light beam 54, preferably about 30% of the light beam 54, is passed by the second beamsplitter 68 and returned to the first assembly 18 by the retro-reflector 70 as a retro-reflected light beam 80. In the first assembly 18, an opacity monitor lens 78 (FIG. 2) collects the retro-reflected light beam 80 and focuses the light onto the opacity monitor 26 to produce the sample light beam intensity, $I_S$, used in Eq. (1).

As best shown in FIG. 5, light entering the second assembly 20 and incident upon the second beamsplitter 68 is directed at the flow rate detector 72. The flow rate detector 72 comprises a flow rate detector lens 82, a third beamsplitter 84 aligned with the flow rate detector lens 82, an upstream detector 86, and a downstream detector 88. The lens 82 of the flow rate detector 72 collects the portion 74 of the light beam 54 that is reflected from the second beamsplitter 68. The third beamsplitter 84 separates the collected light from the flow rate detector lens 82 into the upstream beam 58 and the downstream beam 60. The third beamsplitter 84 preferably separates the collected light from the flow rate detector lens 82 into the upstream beam 58 and the downstream beam 60 with a second pair of polarizers 62 that correspond with the first pair of polarizers. The upstream detector 86 and the downstream detector 88 are positioned at the focal point of the lens 82 of the flow rate detector 72 and respectively measure the intensity of the upstream beam 58 and the downstream beam 60. The polarizers 62 attached to the third beamsplitter 84 ensure that the downstream detector 88 receives only horizontally polarized light and the upstream detector 86 receives only vertically polarized light.

By cross-polarizing the upstream beam 58 and the downstream beam 60 with the polarizers 62, cross-talk between the upstream beam 58 and the downstream beam 60 is eliminated.

Non-homogeneities in the streaming stack gas produce time varying signals at the upstream detector 86 and the downstream detector 88. If the gas flow is laminar, such that any particle in the flow that crossed the downstream beam 60 also crossed the upstream beam 58, the light signal seen by the two detectors would, except for a time displacement $\Delta t$, be identical. In reality, however, the gas flow is turbulent. Consequently, some gas particles passing through the upstream beam 58 do not pass through the downstream beam 60, and vice versa. The time $\Delta t$ required for the flow to travel the $\Delta d$ between the parallel beams is achieved by cross-correlation of the signals, $f(t)$ and $g(t+\Delta t)$, produced by the upstream detector 86 and the downstream detector 88, respectively. This cross-correlation function $C(\Delta t)$, from which $\Delta t$ is determined, can be represented by the relation, $$C(\Delta t)=IFT\{IFT[f(t)]\cdot FT[g(t+\Delta t)]\}, \quad \text{Eq. (4)}$$

where IFT indicates the inverse Fourier transform operation and FT the Fourier transform operation. The symbol • represents the product of the two functions $IFT[f(t)]$ and $FT[g(t+\Delta t)]$. Linear flow velocity V is determined from $$V=\Delta d/\Delta t. \quad \text{Eq. (5)}$$

Volumetric flow rate is obtained by multiplying V, Eq. (5), by the cross-sectional area of the stack 16.

In operation, the emission monitor 12 determines opacity of the gas passing through the stack 16 and determines the flow rate of the gas passing through the stack 16. With respect to determining opacity, when the timing slot 48 (FIG. 3) moves between the aligned light emitter/detector on the timing/calibration wheel assembly 30, circuitry in the first assembly 18 generates a logic "1" optical signal that is sent to the computer in the remote data processor 32 to initiate measurement cycles, as previously mentioned.

After a first preset delay, when the diffuser 50 (FIG. 3) rotates into the sample light beam 54, a diffuser intensity is measured by the opacity monitor 26, and an optically encoded opacity monitor signal $V_D$ is generated and recorded by the remote data processor 32. After a second preset delay, when the crossed-polarizer absorber 52 (FIG. 3) rotates into the sample beam, the opacity monitor 26 measures an offset intensity, and an optically encoded opacity monitor signal $V_A$ is generated and recorded by the remote data processor 32. Since the absorber 52 reflects essentially none of the light incident upon the absorber into the opacity monitor 26, the signal generated is a zero-offset for the opacity monitor circuitry.

After a third preset delay, the opacity monitor 26 measures a retro-reflected intensity, and the remote data processor 32 records the opacity monitor signal $V_S$ of the retro-reflected sample light beam 80 that has traversed the stack 16. This signal is averaged over a time interval, preferably about a 2 second interval. $I_D$ is then determined from $I_D=V_D-V_A$ by the remote data processor 32. The value of $I_D$, when used with the calibration constant in Eq. (3), allows computation of $I_O$ shown in Eq. (1) by the remote data processor 32. Is in Eq. (1) is determined from $I_S=V_S-V_A$ and optical density values determined from Eq. (1) are used with Eq. (2) to calculate opacity in the remote data processor 32.

Upon completion of the opacity measurement, the remote data processor 32 immediately analyses the flow rate data. A plurality of pairs of upstream and downstream flow signals, each of the pairs of flow signals measured during consecutive time intervals by the upstream detector 86 and the downstream detector 88, respectively, are cross-correlated using Eq. (4). Preferably, five pairs of upstream and downstream flow signals, each obtained during consecutive time intervals, are cross-correlated using Eq. (4) by the computer. The time intervals are preferably about 2 second intervals. Each of these cross-correlations is normalized to the highest peak in the cross-correlation function. The 5 normalized cross-correlation functions thus obtained are sequentially summed in an array and stored in computer memory in the remote data processor 32.

The operation described above is repeated for each rotation of the timing wheel 46. The remote data processor 32 may display the opacity obtained each revolution, calculate and display the average opacity over a 5 minute interval, and store the 5 minute average opacity. The 5 minute average opacities are used to compute hourly averages which are also stored. Normalized cross-correlations obtained during successive revolutions of the timing wheel 46 are summed for a predetermined time period by the computer. The time period may be selected to be 5, 10 or 15 minutes. At the end of this time period, the pixel number of the maximum value stored in the array is determined and the array emptied. The pixel number of the maximum value which corresponds to the cross-correlation peak allows for determination of $\Delta t$ in Eq. (5). Because the distance $\Delta d$ between the two orthogonally polarized beams 58, 60 (FIG. 4) is pre-determined during the construction of the emission monitor 12, the average flow rate for the interval is easily computed using Eq. (5) by the computer in the remote data processor 32. The system and method described herein yields opacity and flow rate measurements having minimal error that could arise from the measurement of turbulent flow gases.

ALTERNATIVE EMBODIMENTS

As previously discussed, cross-talk between the upstream and downstream beams is eliminated by cross-polarizing the upstream and downstream beams used to determine flow rate of the stack gases. However, channel isolation of the upstream beam and the downstream beam can also be achieved in other ways. One alternative embodiment uses different wavelengths for the upstream beam and downstream beam. The coherent light beam 54 may be split by the first beamsplitter 42 into an upstream beam having a first wavelength and a downstream beam having a second wavelength. Channel separation at the output of the first beamsplitter 42 is achieved by positioning a first pair of bandpass filters after the first beamsplitter 42. One of the first pair of bandpass filters provides the upstream beam with a first wavelength, the other of the first pair of bandpass filters provides the downstream beam with a second wavelength. To isolate the upstream beam and the downstream beam, one of a second pair of bandpass filters is positioned in front of the upstream detector 86 and the other of the second pair of bandpass filters is positioned in front of the downstream detector 88. The second pair of bandpass filters ensure that the upstream detector 86 receives only light having the first wavelength and the downstream detector 88 receives only light having the second wavelength. Thus, channel isolation of the upstream beam and the downstream beam is produced and maintained by the pairs of bandpass filters.

Figure 9:
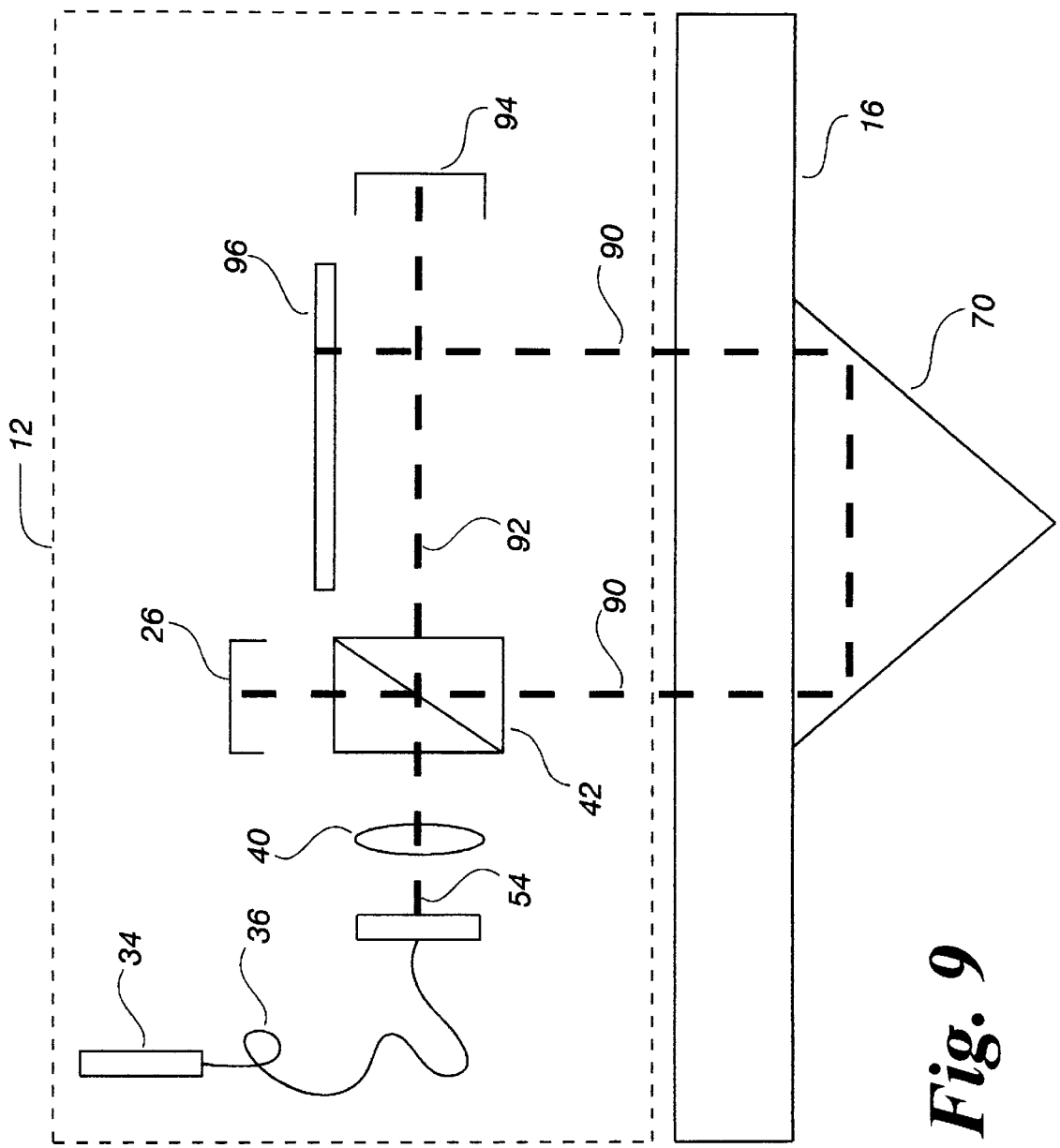
FIG. 9 is a schematic diagram of an alternative embodiment of an emission monitor in a pollutant emissions monitoring system in accordance with the present invention.

As previously described, a two-pass or double-pass optical system is used to measure opacity, meaning that opacity data was collected by the opacity monitor 26 in the first assembly 18 (FIG. 2) after retro-reflection from the second assembly 20 (FIG. 5). Optical configurations utilizing a different number of passes across the stack are possible. FIG. 9 is a schematic diagram of an alternative embodiment of the emission monitor 12 having a 4-pass system. The collimated laser beam 54 is first divided into a sample beam 90 and a reference beam 92 by the first beamsplitter 42. The reference beam intensity is monitored by a reference beam detector 94. The sample beam 90 crosses the stack 16 and is reflected by the retro-reflector 70 onto a plane mirror 96. Upon reflection from the plane mirror 96, the sample beam 90 retraces its path to the first beamsplitter 42. The sample beam intensity is monitored by a sample beam detector 26.

As shown in FIG. 9, the sample beam 90 crosses the stack 16 a total of four times. After the fourth pass, the sample beam 90 strikes the first beamsplitter 42 at the same position the sample beam 90 began its first pass across the stack 16. This embodiment provides excellent stability against vibration and thermally induced misalignment of the stack mounted assemblies. In this embodiment, all active elements (i.e., the first and the second assembly) are mounted on one side of the stack 16. The only element on the opposite side of the stack 16 is the retro-reflector 70. This embodiment provides simple construction and multiplexing of the pollutant emissions monitoring system 10.

EXAMPLE

Figure 6A:
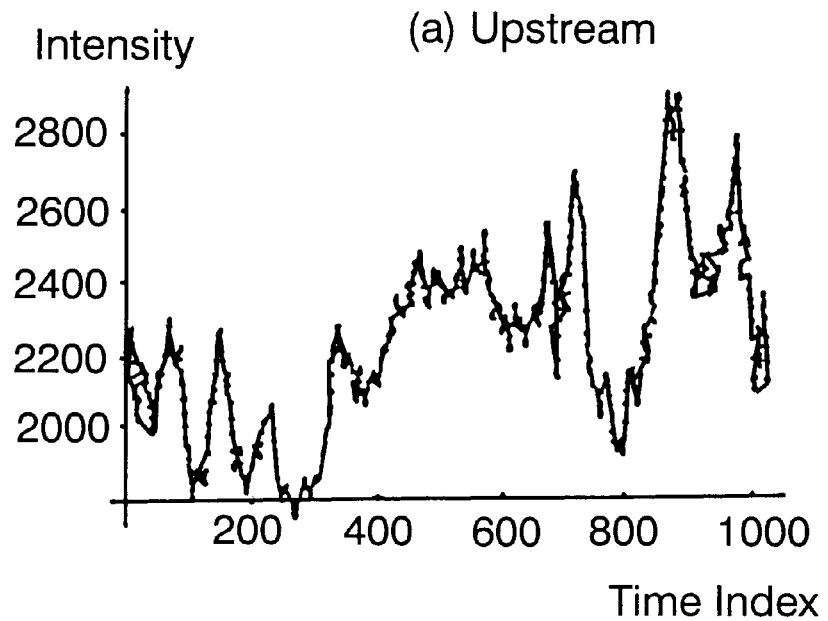
FIG. 6a is a graph depicting flow rate signals in a 6 inch/15.24 cm stack from an upstream flow rate detector.
Figure 6B:
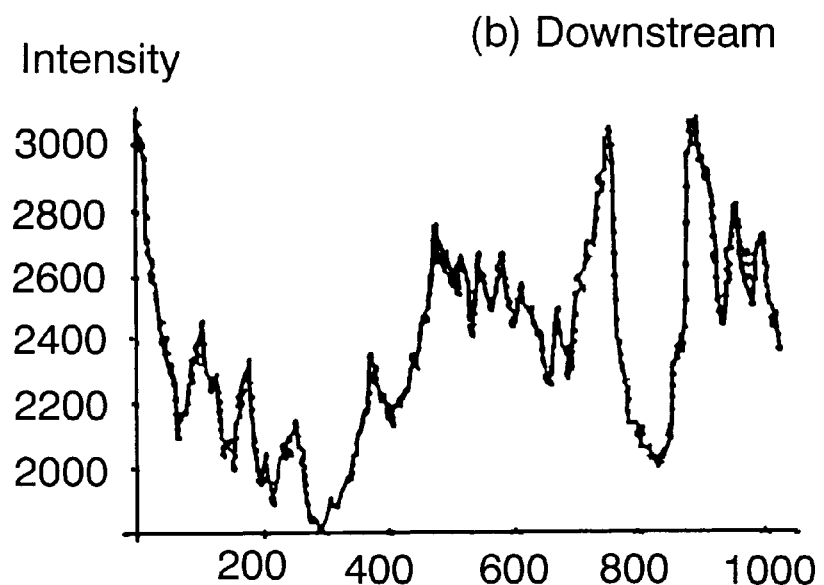
FIG. 6b is a graph depicting flow rate signals in a 6 inch/15.24 cm stack from a downstream flow rate detector.
Figure 7A:
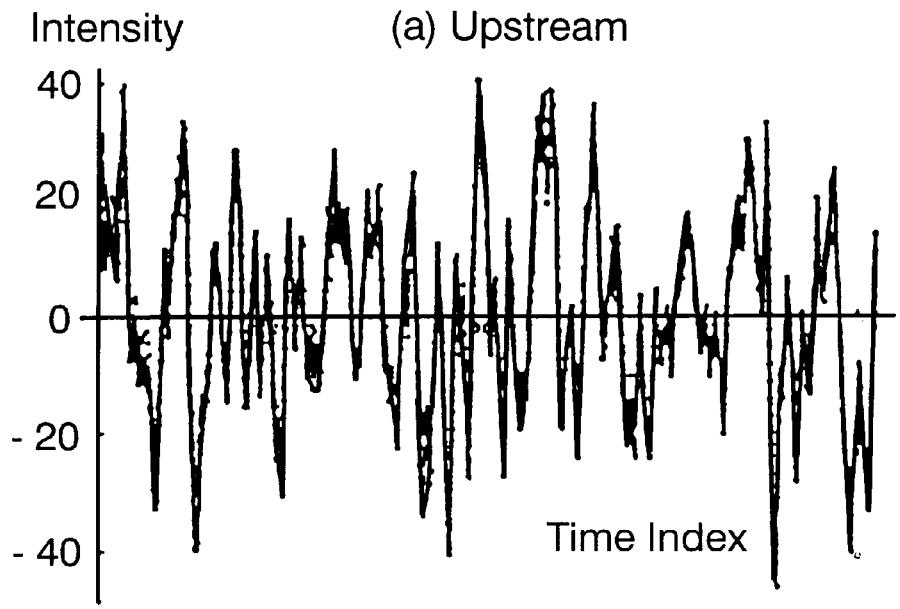
FIG. 7a is a graph depicting flow rate signals in a 18 foot/5.48 meter stack from an upstream flow rate detector.
Figure 7B:
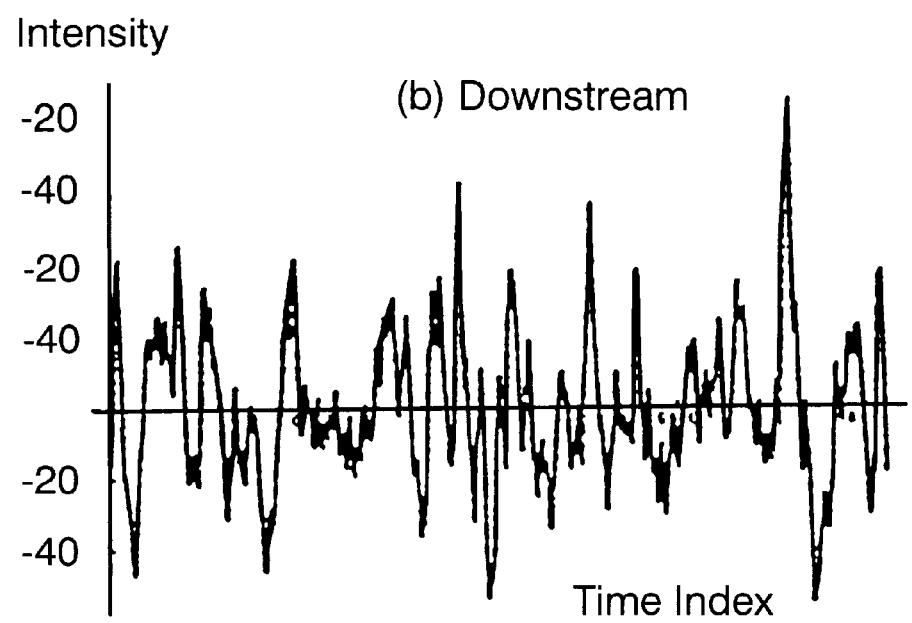
FIG. 7b is a graph depicting flow rate signals in a 18 foot/5.48 meter stack from a downstream flow rate detector.
Figure 8A:
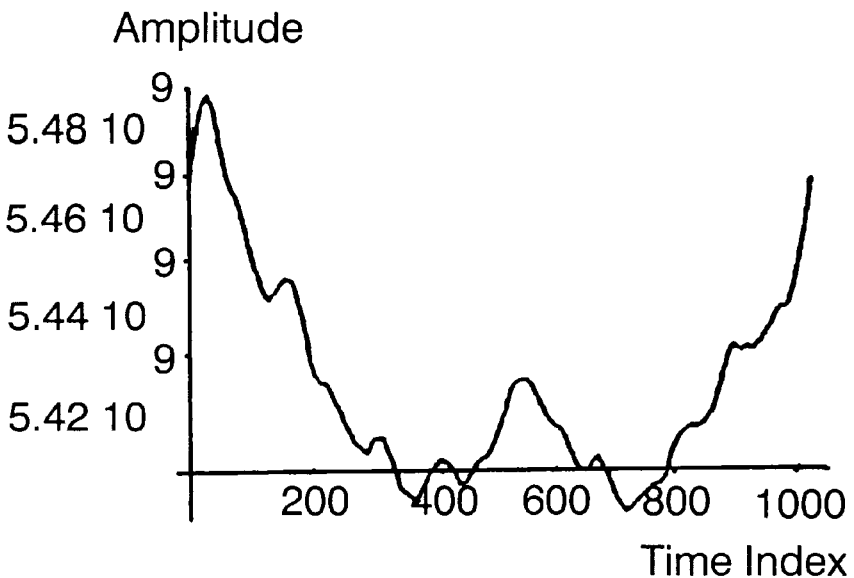
FIG. 8a is a graph depicting the cross-correlation function for the flow rate signals depicted in FIGS. 6a and 6b.
Figure 8B:
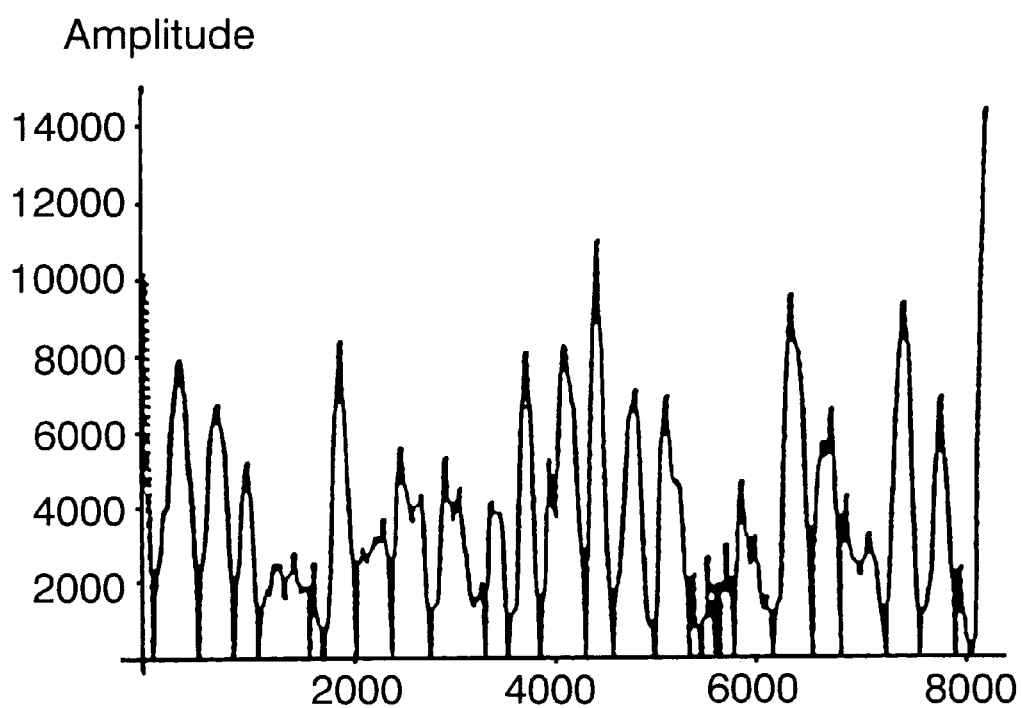
FIG. 8b is a graph depicting the cross-correlation function for the flow rate signals depicted in FIGS. 7a and 7b.

Flow rate detector signals obtained in a 6-inch line-of-sight stack having a turbulent medium are shown in FIGS. 6a and 6b. Similar signals obtained in an 18-foot line-of-sight stack operated by Duke Power Company at Allen Steam Plant in Belmont, N.C., are shown in FIGS. 7a and 7b. Flow rate data (e.g., the intensities of the light beams) is extracted from the beam after the first pass across the stack because the flow of gases in the stack involves severe turbulence. In situations involving more laminar flow, flow rate data is extracted after two, or possibly more, passes across the stack. Because of stack turbulence, the upstream and downstream signals are not identical in either FIG. 6a or FIG. 6b. Even so, a casual examination shows that the downstream signal shown in FIG. 6b is correlated in time with the upstream signal in FIG. 6b. However, due to a greater turbulence in the stack flow at Allen Steam Plant, the time displacement between the upstream and the downstream signals in FIGS. 7a and 7b is not as apparent as for the 6-inch stack signals shown in FIGS. 6a and 6b. In both cases, however, the time $\Delta t$ required for the flow to travel the $\Delta d$ between the parallel beams is achieved by cross correlation of the signals, $f(t)$ and $g(t+\Delta t)$, produced by the upstream and downstream detectors, respectively. Cross-correlation functions for the upstream-downstream signal pairs shown in FIGS. 6a and 6b and FIGS. 7a and 7b are respectively displayed in FIGS. 8a and 8b.

SUMMARY OF THE ACHIEVEMENT OF THE OBJECTS OF THE INVENTION

From the foregoing, it is readily apparent that we have invented an emissions monitoring system that measures opacity and flow rate of pollutant emissions using entirely optical based monitors. The present invention provides a two-pass pollution emissions monitoring system having a continuously recording opacity monitor that exhibits excellent stability against noise and signal drift resulting from vibrations and thermally induced expansion within the system being monitored. The present invention provides an optical based flow monitor that measures variable flow velocities of gases passing through a stack having laminar or turbulent characteristics. The present invention provides an optical based pollutant emissions monitoring system having an opacity/flow rate monitor that is stack-mounted as a single unit. The present invention provides a pollutant emissions monitoring system that is substantially immune to damage caused by lightning and electrical surge, particularly from lightning strikes on or near a stack. The present invention provides a method of measuring opacity and flow velocities of pollutant emissions that naturally yields line of sight averages as opposed to measurements at a point.

It is to be understood that the foregoing description and specific embodiments are merely illustrative of the best mode of the invention and the principles thereof, and that various modifications and additions may be made to the apparatus by those skilled in the art, without departing from the spirit and scope of this invention, which is therefore understood to be limited only by the scope of the appended claims.

What is claimed is:

1. A pollutant emissions monitoring system for stack gases passing through a stack having a pair of diametrically opposed stack penetrations said system comprising:

an entirely optical-based emission monitor mounted on the stack for measuring opacity and flow rate of gas passing through the stack, said emission monitor comprising:

a first assembly for generating optical signals having an opacity monitor and a light beam assembly, said first assembly positionable in one of the stack penetrations, said first assembly having means for encoding the generated optical signals; and a second assembly for monitoring flow rate, said second assembly positionable across from said first assembly and in the opposing stack penetration, said second assembly having means for decoding the encoded optical signals from said first assembly;

a fiber optic cable connected to said emission monitor for conducting optical data; and a remote data processor optically connected to said emission monitor by said fiber optic cable for receiving optical data from said emission monitor, said remote data processor determining the opacity and the flow rate of gas passing through the stack based on the encoded and decoded optical signals from said first assembly and said second assembly;

wherein said remote data processor determines the weight of fly ash in the stack gases based on the opacity and the flow rate.

2. A pollutant emissions monitoring system according to claim 1 wherein said emission monitor comprises:

a first assembly having an opacity monitor and a light beam assembly; and a second assembly for monitoring flow rate, said first assembly positioned diametrically across from said second assembly on the stack.

3. A pollutant emissions monitoring system according to claim 2 wherein said light beam assembly comprises:

a light source for generating a collimated light beam;

a wheel assembly optically connected to said remote data processor for initiating measurement cycles and calibrating said opacity monitor; and a first beamsplitter for receiving and splitting the collimated light beam from said wheel assembly into an upstream beam and a downstream beam.

4. A pollutant emissions monitoring system according to claim 3 wherein said wheel assembly comprises:

a synchronous motor generating a pre-determined constant rate of revolution;

a timing wheel fixed to said synchronous motor having a front side, a back side and a timing slot; and a light emitter/detector for generating an optical signal corresponding to each revolution of said motor having an emitter portion facing the front side of said timing wheel and a detector portion facing the back side of said timing wheel and aligned with the emitter portion and the timing slot.

5. A pollutant emissions monitoring system according to claim 4 wherein said wheel assembly further comprises a diffuser mounted on said timing wheel; and an optical absorber mounted on said timing wheel, said diffuser and said absorber of said timing wheel for producing optical signals for real-time calibration of said opacity monitor.

6. A pollutant emissions monitoring system according to claim 4 wherein said constant rate of revolution of said synchronous motor is about 2 revolutions/minute.

7. A pollutant emissions monitoring system according to claim 3 wherein said second assembly comprises:

a second beamsplitter for reflecting a portion of the light beam from said first assembly and passing a remainder of the light beam from said first assembly;

a retro-reflector aligned with said second beamsplitter for returning the passed light from said second beamsplitter to said first assembly; and a flow rate detector for receiving the reflected light from said second beamsplitter and detecting the intensity of the reflected portion of the light beam.

8. A pollutant emissions monitoring system according to claim 7 wherein said portion of the light beam from said first assembly is about 70%.

9. A pollutant emissions monitoring system according to claim 7 wherein said remainder of the light beam from said first assembly is about 30%.

10. A pollutant emissions monitoring system according to claim 7 wherein said flow rate detector comprises:

a lens for collecting light reflected from said second beamsplitter;

a third beamsplitter aligned with said lens for splitting the collected light from said lens into the upstream beam and the downstream beam;

an upstream detector positioned at a first focal point of said lens for measuring the intensity of the upstream beam; and a downstream detector positioned at a second focal point of said lens for measuring the intensity of the downstream beam.

11. A pollutant emissions monitoring system according to claim 10 wherein said light beam assembly further comprises a first pair of polarizers for orthogonally polarizing the upstream beam and the downstream beam.

12. A pollutant emissions monitoring system according to claim 11 wherein said third beamsplitter further comprises a second pair of polarizers corresponding to said first pair of polarizers of said light beam assembly, said second pair of polarizers for separating the upstream beam and the downstream beam.

13. A pollutant emissions monitoring system according to claim 10 wherein said light beam assembly further comprises a first pair of bandpass filters, one of said first pair of bandpass filters for providing the upstream beam with a first wavelength, the other of said first pair of bandpass filters for providing the downstream beam with a second wavelength.

14. A pollutant emissions monitoring system according to claim 13 wherein said flow rate detector further comprises a second pair of bandpass filters, one of said second pair of bandpass filters for isolating the upstream beam with the first wavelength, the other of said second pair of bandpass filters for isolating the downstream beam with the second wavelength.

15. A pollutant emissions monitoring system according to claim 3 wherein said light source comprises:

a diode laser;

a single mode optical fiber coupled to said diode laser;

a positioner connected to said single mode optical fiber for receiving light from said diode laser and directing the received light to a pre-determined position across the stack; and a lens positioned to collimate light directed by said positioner.

16. A method of monitoring pollutant emissions from gas passing through a stack with an entirely optical-based emission monitor for measuring opacity and flow rate using coded optical signals and a remote data processor connected to the emission monitor by fiber optic cable for receiving optical data from the emission monitor and determining the opacity and the flow rate of gas passing through the stack and the weight of fly ash in the gas based on the opacity and the flow rate, the emissions monitor comprising a light source for producing a light beam, a retro-reflector for reflecting the light beam and a wheel assembly comprising a motor, a timing wheel, a diffuser and an absorber, the method comprising the steps of determining opacity of the gas passing through the stack with the emission monitor; and determining flow rate of the gas passing through the stack with the emission monitor.

17. A method of monitoring pollutant emissions according to claim 16 wherein the step of determining opacity comprises the steps of periodically generating a logic optical signal for each revolution of the timing wheel;

measuring a diffuser intensity when the diffuser rotates into the light beam;

measuring an offset intensity when the absorber rotates into the light beam;

measuring a retro-reflected intensity of the retro-reflected light beam; and calculating optical density values and opacity based on the diffuser intensity, the offset intensity and the reflected intensity.

18. A method of monitoring pollutant emissions according to claim 16 wherein the step of determining flow rate of gas comprises the steps of measuring a plurality of pairs of upstream and downstream flow signals, each of the flow signals are measured during consecutive time intervals;

correlating each of the plurality of pairs of flow signals;

normalizing the correlated flow signals;

summing the normalized flow signals in sequence for a predetermined time period; and storing the summed flow signals.

19. A method of monitoring pollutant emissions according to claim 18 wherein the step of summing is performed for a time period selected from the group consisting of 5, 10 and 15 minutes.

20. A method of monitoring pollutant emissions according to claim 18 wherein the step of measuring is performed during consecutive 2 second intervals.

* * * * *